United States Patent [19]

Schwarz et al.

[11] 4,041,276
[45] Aug. 9, 1977

[54] ELECTRIC FLUID HEATING DEVICE

[75] Inventors: Werner Schwarz; Eugen Hohmann, both of Heppenheim; Bernd Nickel, Bensheim, all of Germany

[73] Assignee: Siemens Aktiengesellschaft, Munich, Germany

[21] Appl. No.: 413,268

[22] Filed: Nov. 6, 1973

[30] Foreign Application Priority Data

Nov. 14, 1972   Germany ............................... 2255736

[51] Int. Cl.² .......................... H05B 1/02; F24H 1/12; A61F 7/00
[52] U.S. Cl. ..................................... 219/308; 128/254; 219/302; 219/328; 219/379; 219/501; 219/505; 222/146 HE
[58] Field of Search ............... 219/214, 209, 210, 501, 219/296–309, 373, 379, 327–331, 504, 505; 128/224, 254–257; 222/146 HE, 146 R

[56] References Cited

U.S. PATENT DOCUMENTS

| | | | |
|---|---|---|---|
| 3,121,426 | 2/1964 | Yoshida | 219/373 UX |
| 3,300,623 | 1/1967 | Smyrnos | 219/210 X |
| 3,308,271 | 3/1967 | Hilbiber | 219/501 |
| 3,320,407 | 5/1967 | Holmes | 219/210 UX |
| 3,330,941 | 7/1967 | Del Duca | 219/501 |
| 3,333,086 | 7/1967 | Williams | 219/210 UX |
| 3,393,870 | 7/1968 | Jeffrey | 219/501 X |
| 3,413,438 | 11/1968 | Gardner et al. | 219/10 |
| 3,450,863 | 6/1969 | Scholl | 219/501 |
| 3,517,162 | 6/1970 | Webb | 219/501 X |
| 3,588,467 | 6/1971 | Grosjean | 219/302 X |

*Primary Examiner*—A. Bartis
*Attorney, Agent, or Firm*—Allison C. Collard

[57] ABSTRACT

An electric fluid heating device for heating comparatively small amounts of a fluid medium, particularly for dental purposes, is characterized in that an operable controllable semiconductor, such as a transistor, is used as the heating element. The fluid heating device includes a metallic casing provided with a fluid heating chamber having a fluid inlet and outlet. The semiconductor is seated in a recess in the casing in heat exchange relation with the chamber. A temperature responsive control circuit including a PTC resistor in heat exchange relationship with the chamber is provided for regulating the current flowing through the semiconductor and thus the heat output thereof. The casing is made in two parts to permit a damaged smiconductor to be easily removed and replaced.

3 Claims, 3 Drawing Figures

ELECTRIC FLUID HEATING DEVICE

This invention relates to an electrical heating device for heating comparatively small amounts of a medium, particularly for dental purposes.

Heating devices are known wherein so-called heating cartridges are used. The heating cartridges consist substantially of a ceramic casing in which is isolatedly located a glow coil adapted to be connected to a source of voltage. These heating devices are comparatively large, particularly for larger heat outputs, so that it is rather difficult to place them in small baffle spaces. A further drawback is that the regulating of temperature of the medium to be heated with such a heating device is not satisfactory and is possible only through a comparatively large expenditure for additional structural parts (bimetallic regulator, etc.) which in addition constitute a further source of wear.

An object of the present invention is the provision of an electrical heating device of the described type which is of simple construction, which can be made very small in size and which makes possible a particular good regulation of temperature of the medium to be heated without requiring a larger amount of structural parts.

In the accomplishment of the objectives of the present invention it was found desirable to use an operable semiconductor as the heating element. Of advantage is the use of a transistor.

Up to now the lost heat taking place in a transistor or other operable semi-conductor was always considered as undesirable. Measures were carried out with correspondingly large expenditure and often by adopting substantial compromises to direct heat appearing in these semi-conductors as quickly as possible to the surrounding air. Transistors are purposefully arranged, for example, in well cooled locations of an apparatus or within a switching device. Additional means, such as cooling ribs or heat removing sheets were used to provide a better and quicker heat transfer into the open.

The present invention is based on the idea of deliberately using the heat of an operable semi-conductor which up to now was removed unused with large expenditure and to employ it for heating a medium. The present invention provides a heating device which is simply constructed, which can be placed in small baffle spaces and which particularly provides good regulation of temperature of the medium to be heated. This can be attained by operating the transistor with an actuating member dependent on temperature. Since a transistor can be easily regulated comparatively simple means can provide a very good and precise temperature regulation for the medium to be heated. As the operating member a PTC resistor can be advantageously used. The heating device is thus made as a self regulating heater. At low temperatures the PTC resistor opens the transistor and thus switches on the heating. With increasing temperature the transmittancy of the transistor is diminished more and more until finally it is locked completely and thus switches off the heating device. In order to be able to compensate for larger leakage in transistors which would lead to excessively high collective currents in transistors, it is advantageous to provide a series resistance connected in series with the collector-emitter stretch of the transistor to limit the collector current, the voltage potential of which influences an operating transformer for operating the basic current of the transistor.

The invention will appear more clearly from the following detailed description when taken in connection with the accompanying drawing showing by way of example only, preferred embodiments of the inventive idea.

Figure 1:
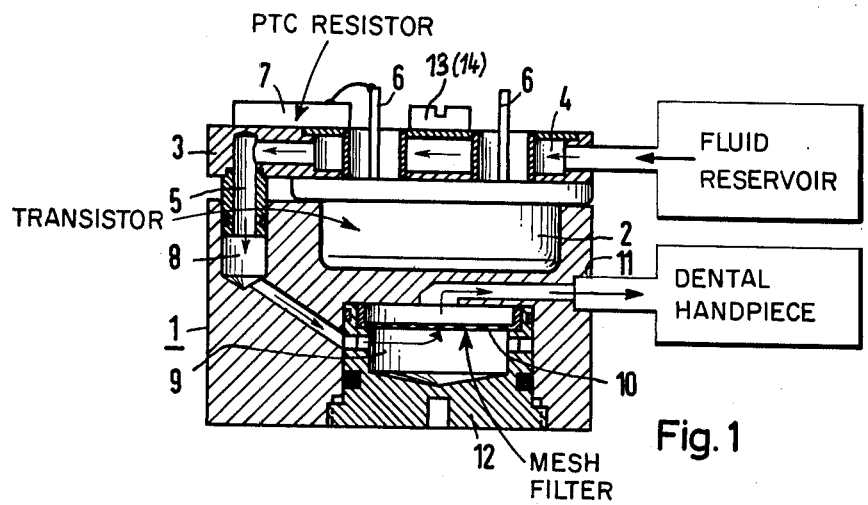
FIG. 1 is a section through an electrical heating device of the present invention.

FIG. 1 shows an electrical heating device used for the heating of a flowing liquid medium. The heating device includes a heating block 1 made of a good heat conducting material, for example, of brass. At its upper side a transistor 2 is placed lowered in a corresponding countersink. The mass of the heater block is so set that on the one hand there is a sufficiently great heat capacity and on the other hand a good regulation of the temperature of the medium to be heated can be produced. The outer surface of the heater block can be covered with an insulating coating, thereby increasing the efficiency of the heating device. An effective shape of the heater block, for example, a ball, can also help in diminishing the outward passage of heat and thereby improve the efficiency of the heater.

The transistor 2 is connected by its pot-like casing with the heater block 1, possibly with the provision of a heat conducting paste, so as to provide good heat transmission. A cover 3 lies upon the transistor 2 and contains a chamber 4 and a channel 5. Electrical contacts 6 of the transistor 2 extend with insulation out of the cover 3. Cold medium flowing into the chamber 4 absorbs the heat produced by the transistor. Since the transistor is most strongly heating within the range of its electrical contacts 6 and since the cover 3 is comparatively thin walled and consists of a good heat conducting material, a great transmission of heat to the medium takes place in the chamber 4. A PTC resistor 7 is provided on the top side of the cover 3 and lies firmly upon the outer surface of the cover, possibly again with the use of an intermediate layer of heat conducting paste. The medium heated in the chamber 4 flows through channels 5, 8 into a chamber 9 from which it reaches the outflow channel 11 through a mesh filter 10. The mesh filter 10 prevents small particles possibly contained in the flowing medium from clogging the outflow openings, which are often very small, of the users connected to the outlet. The filter 10 can be easily replaced or removed for cleaning by the removal of a closing screw 12. When suitable material is provided for the casing of the transistor it can be also directly rinsed by the flowing medium. This considerably improves the heat exchange and also the regulation of the heating device.

The cover 3 is pressed by two screws 13, 14 against the underlying surface of the transistor 2, so that there is a good heat transmission between the two parts. It is also possible to further improve heat transmission by the use of an intermediate layer of a heat conducting paste. If the transistor is damaged, it can be easily removed from the heat block 1 and replaced by a new one.

As a variant it is also possible to use an output transistor in the shape of a small plate, namely, without the pot-like casing. This construction is particularly well suited for insertion of the heating device into a dental handpiece.

Figure 2:
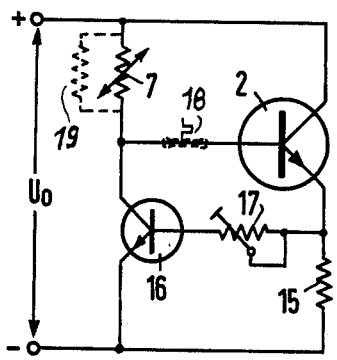
FIG. 2 is an electrical switch circuit of the same heating device.

FIG. 2 shows the switch circuit of the heating device. To a source of direct voltage $U_o$ are connected in series the collector-emitter part of the transistor 2 which is an output transistor, and a series-resistance 15. Parallel thereto and also in series extend the PTC resistor 7 and the collector-emitter part of an control transistor 16. A regulatable resistance 17 extends between the base of the control transistor 16 and the emitter of the output transistor 2. The control transistor 16 and the two resistances 15 and 17 are mounted upon a conducting plate (not shown) which is arranged at the rear side of the heating block 1 and spaced from the block.

Figure 3:
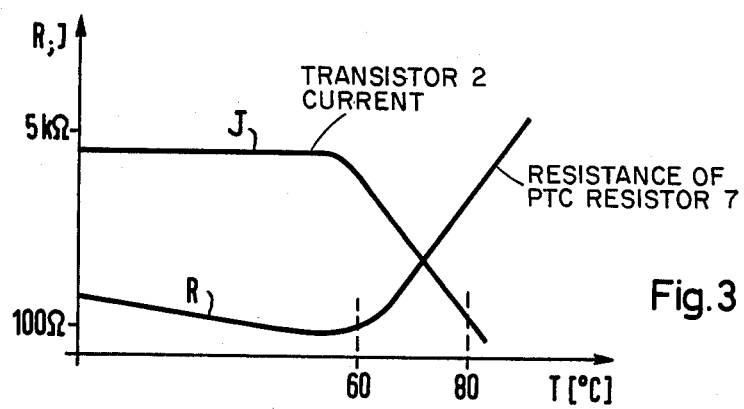
FIG. 3 shows operational diagrams.

The PTC resistor 7 supplies the necessary basic current to the output transistor 2 and produces the self regulation of the heating device. When there is a great flow of water and the water temperature is cold, the transistor 2 has a high output reception, as indicated in the diagram of FIG. 3 by the current flow J. The current value is about 4A. At a specific temperature of the PTC resistor 7, for example 60° C, it will become high impedance, as indicated by the resistance line R in FIG. 3. The result is that the collector current and the loss output of the output transistor 2 are reduced.

The value of the PTC resistor is so selected that with an output transistor with the smallest current amplification, a collector current of about 4A can flow. Due to the comparatively great dispersion of the transistors with respect to their current amplification, it is necessary to provide a current limitation. This current limitation is taken over by the series-resistance 15 and the regulatable resistance 17. The collector-emitter current of the output transistor 2 develops at the series-resistance 15 having about 0.22 ohm resistance a voltage which controls the control transistor 16 when a certain value is exceeded. Thus the basic current of the output transformer 2 is diminished to such an extent that the control transistor 16 will be closed through the series-resistance 15 by the diminution of the voltage drop. This produces an equilibrium which continues until the PTC resistor 7 has a different temperature. Due to the thin walls of the cover 3 changes in temperature of the flowing medium are comparatively quickly received by the PTC resistor 7 and are transmitted to the heating member, namely, the output transistor 2.

According to a further advantageous embodiment of the present invention a still faster temperature regulation can be produced when the actuating member, namely, the PTC resistor is located in the transmitting channel of the medium to be heated. The start of current limitation can be set with the regulatable resistance 17. This greatly compensates for losses in the transistors which are unavoidable during the mounting of the heater.

It is also within the framework of the present invention to use as the heating element a different operable semi-conductor instead of the described transistor. A thermo-switch can be also used as the actuating member dependent on temperature. This possibility is shown by broken lines in FIG. 2. The thermoswitch indicated as 18 and 19 is a fixed resistance which replaces the PTC resistor 7. It is also possible to use a regular conductor by suitably changing the switch circuit shown in FIG. 2.

The heating device of the present invention can be used in dental work, for example, for heating spray water and/or air which are transmitted into a handpiece, such as a boring or spraying handpiece or the like. It is particularly advantageous to provide the heating device within the handpiece. The heat conduit due to its short length and consequently small cooling of the heated medium up to the treating location does not have to be as long as would have been the case if the heating device were placed in a part located away from the handpiece.

What is claimed is:

1. An electrical heating device in dental instruments for heating small amounts of a fluid medium, said device comprising a casing consisting of a material with a good thermal conductivity and having an inlet, an outlet and an inner chamber connected with said inlet and said outlet, said chamber being adapted to receive the fluid medium to be heated, a heating element consisting of a controllable semi-conductor, means having a temperature responsive operating member mounted in thermal contact with said casing, said semi-conductor comprising a load output for current flow therethrough when connected to a source of voltage and a control input, and connecting means electrically connecting said control input with said temperature responsive operating member for controlling said current flow, wherein said casing consists of two parts located one on top of the other, the first part of the casing having a recess receiving said semi-conductor, the second part of the casing containing said inner chamber and supporting said operating member determining the temperature of the medium, said semi-conductor having casing surfaces and having upon a casing surface electrical contacting connections extending through the second part of the casing while being insulated therefrom and electrically connected with said semi-conductor, said second part of the casing being thermally connected with said casing surface.

2. A heating device according to claim 1, wherein said semi-conductor has a further casing surface opposed to its connections and sunk in said recess in the first part of the casing, the first-mentioned casing surface of the semi-conductor which carries the electrical connections being directed toward said chamber and being thermally connected with said first part of the casing.

3. A heating device according to claim 1, wherein both parts of the casing consist of brass, and wherein both parts, when mounted one on top of the other, have an outer block shape.

* * * * *